(12) United States Patent
Fürstner et al.

(10) Patent No.: US 6,525,197 B1
(45) Date of Patent: Feb. 25, 2003

(54) METHODS FOR PREPARING MACROCYCLIC PRODUCTS BY RING-CLOSING DIYNE METATHESSIS

(75) Inventors: Alois Fürstner, Mülheim an der Ruhr (DE); Günter Seidel, Oberhausen (DE); Antonio Rumbo, Mülheim an der Ruhr (DE); Christian Mathes, Mülheim an der Ruhr (DE)

(73) Assignee: Studiengesellschaft Kohle mbH, Mulheim an der Ruhr (DE)

( * ) Notice: Subject to any disclaimer, the term of this patent is extended or adjusted under 35 U.S.C. 154(b) by 0 days.

(21) Appl. No.: 09/601,632

(22) PCT Filed: Feb. 2, 1999

(86) PCT No.: PCT/EP99/00674

§ 371 (c)(1),
(2), (4) Date: Aug. 4, 2000

(87) PCT Pub. No.: WO99/40047

PCT Pub. Date: Aug. 12, 1999

(30) Foreign Application Priority Data

Feb. 6, 1998 (DE) .......................... 198 04 673

(51) Int. Cl.$^7$ ...................... A61K 31/33; A61K 31/335; C07D 401/00; C07D 225/00; C07D 221/00
(52) U.S. Cl. ...................... 544/310; 540/450; 540/451; 540/460; 546/112; 546/113; 546/115; 546/116; 546/120; 514/183; 514/211; 514/218; 514/277; 514/299; 514/302; 514/450; 514/430; 514/431
(58) Field of Search .................. 549/266; 540/450, 540/451, 460; 546/112, 113, 115, 116, 120; 514/183, 211, 218, 277, 299, 302, 450, 430, 431; 544/310

(56) References Cited

PUBLICATIONS

A. Furstner: "Conformationally unbiased macrocyclization reactions by ring closing metathesis" Journal of Organic Chemistry, Bd. 61 Nr. 12, 1996, Seiten 3942–3943, XP002077144 Easton US.

P. Bertinato: "Studies toward a synthesis of epothilone A: stereocontrolled assembly of the acyl region and models for macrocyclization" Journal of Organic Chemistry, Bd. 61, Nr. 23, 1996, Seiten 8000–8001, XP002077143 Easton US siehe das ganze Dokument.

J. Boivin: "An efficient synthesis of large ring acetylene" Tetrahedron Letters, Bd. 36, Nr. 32, 1995, Seiten 5737–5740, XP002103896 Oxford GB, siehe Seite 5737–Seite 5738.

A. Furstner: "Ring–closing metathesis of functionalized acetylene derivatives: a new entry into cyloalkynes" Angewandte Chemie International Edition, Bd. 37, Nr. 12, 3.Juli 1998, Seiten 1734–1736, XP0021038897 Weinheim DE siehe das ganze Dokument.

Fuerster et al, "Olefin Metathesis . . . ", Angew. Chem. Intl. Edn., 36/22,2466–2468(1997).*

"Organic Chemistry", Morrison & Boyd, pp. 560–561 (1983).*

Fuerster et al, "Olefin Metathesis . . . "; Angew.Chem. Int.Edn., 36/22 pp. 2466–2468(1997).*

J.H.Wengrovius et al "Metathesis of Acetylenes by W(VI)";J. Am Chem. Soc.97, 1592–94(1975).*

* cited by examiner

*Primary Examiner*—Richard L. Raymond
*Assistant Examiner*—Sudhaker B Patel
(74) *Attorney, Agent, or Firm*—Norris McLaughlin & Marcus

(57) ABSTRACT

The present invention relates to methods for preparing macrocyclic products having 9 or more ring atoms by ring-closing diyne metathesis of suitable diyne substrates. The diyne substrates can be converted into cycloalkynes or into cycloalkadiynes by cyclodimerization, depending on the particular reaction conditions. Any alkyne metathesis catalyst can be used as the catalyst, regardless of whether said catalysts are heterogeneously or homogeneously present in the reaction medium. The preferred catalysts or pre-catalysts are transition metal alkylidyne complexes, transition metal compounds which form alkylidyne complexes under the reaction conditions, and transition metal compounds with metal-metal triple bonds. The method can be carried out with numerous functional groups, solvents, and additives. Using known methods, the formed macrocyclic cycloalkynes or cycloalkadiynes can be converted into numerous secondary products, especially macrocyclic cycloalkenes with a uniform configuration of the double bond, and used, e.g., for the synthesis of epothilone or epothilone analogues.

30 Claims, No Drawings

METHODS FOR PREPARING MACROCYCLIC PRODUCTS BY RING-CLOSING DIYNE METATHESSIS

This application is a 371 of PCT/EP99/00674, filed on Feb. 2, 1999.

The present invention pertains to methods for preparing macrocyclic products having 9 or more ring atoms by a ring-closing metathesis of diyne substrates.

By alkyne metathesis there is understood the mutual transalkylidynation of alkynes according to scheme 1.

Scheme 1
The principle of alkyne metathesis

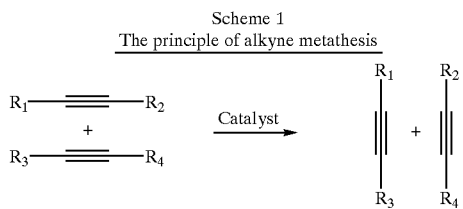

Usually, reactions of this type are catalyzed by metal compounds (reviews: Schrock, R. R. *Polyhedron* 1995, 14, 3177; Ivin, K. J.; Mol, J. C. *Olefin Metathesis and Metathesis Polymerization*, Academic Press, New York, 1997, p 192–223). Contrary to the metathesis of alkenes, which is a well-established field of research today and has found numerous applications in the preparation of technically important products (reviews: Ivin, K. J.; Mol, J. C. *Olefin Metathesis and Metathesis Polymerization*, Academic Press, New York, 1997; Schuster, M. et al., *Angew. Chem.* 1997, 109, 2125), in organic chemistry the application of the alkyne metathesis is restricted to the preparation of special polymers (Weiss, K. et al., *Angew. Chem.* 1997, 109, 522), the ring-opening polymerization of cycloalkynes (Krouse, S. A. et al., *Macromolecules* 1989, 22, 2569; Zhang, X-P. et al., *Macromolecules* 1994, 27, 4627) and the dimerization or the cross metathesis of acyclic alkynes (Kaneta, N. et al., *Chem. Lett.* 1995, 1055; Sancho, J. et al., *J. Mol. Cat.* 1982, 15, 75; Villemin, D. et al., *Tetrahedron Lett* 1982, 5139). The metatheses of diynes result in polymeric products by acyclic diyne metathesis (Krouse, S. A. et al., *Macromolecules* 1989, 22, 2569) or by cyclopolymerization (Fox, H. H. et al. *J. Am. Chem. Soc.* 1994, 116, 2827; Koo, K.-M. et al., *Macromolecules* 1993, 26, 2485).

Both heterogeneous and homogeneous transition metal compounds can be used as catalysts or pre-catalysts for alkyne metatheses. Transition metal alkylidyne complexes and transition metal carbyne complexes which may either be added to the reaction mixtures in isolated form or formed in situ from suitable pre-catalysts are regarded as catalytically active species (Katz, T. J. et al., *J. Am. Chem. Soc.* 1975, 97, 1592). The catalytic activity of transition metal compounds in alkyne metatheses can be increased by the addition of suitable additives such as, e.g., phenol derivatives (Mortreux, A. et al., *J. Chem. Soc. Chem. Commun.* 1974, 786; Mortreux, A. et al., *J. Mol. Cat.* 1977, 2, 73; Villemin, D. et al., *Tetrahedron Lett.* 1982, 5139), aluminium alkyls (Petit, M. et al., *J. Chem. Soc. Chem. Commun.* 1982, 1385), or $SiO_2$ (Mortreux, A. et al., *Bull. Soc. Chim. Fr.* 1972, 1641; Mortreux, M. et al. *J. Mol. Cat.* 1980, 8, 97).

Preferred catalysts or pre-catalysts for alkyne metatheses are $Mo(CO)_6$ (Mortreux, A. et al., *J. Chem. Soc. Chem. Commun.* 1974, 786; Mortreux, A. et al., *J. Mol. Cat.* 1977, 2, 73; Villemin, D. et al, *Tetrahedron Lett* 1982, 5139; Tsonis, C. React. *Kinet. Catal. Lett.* 1992, 46, 359), $MoO_2(acac)_2/Et_3Al$ (Petit, M. et al., *J. Chem. Soc, Chem. Commun.* 1982, 1385), $MoO_3/SiO_2$ (Mortreux, A. et al., *Bull. Soc. Chim. Fr.* 1972, 1641; Mortreux, M. et al. *J. Mol. Cat.* 1980, 8, 97), $WoO_3/SiO_2$ (Pennella, F. et al., *Chem, Commun* 1968, 1548), $W(\equiv CCMe_3)(OR)_3$ or $Mo(\equiv CCMe_3)(OR)_3$ [$R=CMe_3$, $CH(CF_3)_2$, $CMe_2CF_3$, $CMe(CF_3)_2$, $C(CF_3)_3$, $C_6H_3Me_2$, $C_6H_3i-Pr_2$, $C_6H_3t-Bu_2$] (Review: Schrock, R. R., *Polyhedron* 1995, 14, 3177; Sancho, J. et al., *J. Mol. Cat.* 1982, 15, 75; Weiss, K. in *Carbyne Complexes* [Fischer, H. et al., Eds.], Verlag Chemie, Weinheim, 1988, p 220), $Re(\equiv CCMe_3)(=NAr)[OCMe(CF_3)_2]_2$ (Schrock, R. R. et al., *J. Am. Chem. Soc.* 1988, 110, 2686; Weinstock, I. A. et al., *J. Am. Chem. Soc.* 1991, 113, 135), $(Me_3CO)_3W\equiv W(OCMe_3)$ or $(Me_3CO)_3Mo\equiv Mo(OCMe_3)$ (Schrock, R. R. *Polyhedron* 1995, 14, 3177; Krouse, S. A. et al., *Macromolecules* 1989, 22, 2569; Zhang, X-P. et al., *Macromolecules* 1994, 27, 4627) and complexes containing a $Re\equiv Re$ triple bond (Diefenbach, S. P. U.S. Pat. No. 4,698,451, 06. Okt. 1987; Chem. Abstr. 1988, 108, 40092 m).

In the literature both diynes and cycloalkynes have only been used as starting materials for polymerization reactions via alkyne metathesis. Surprisingly, however, we have found that diynes having suitable chain lengths used as substrates can be closed in the presence of suitable catalysts with a high selectivity to yield cycloalkynes, provided the formed cycloalkynes have 12 or more ring atoms (scheme 2).

Furthermore, it turned out that diynes having suitable chain lengths and used as substrates can also be closed with high selectivity to yield cycloalkynes having from 9–11 ring atoms, provided the diyne substrates are conformationally pre-organized for the ring closure by one or several structural elements. Said structural elements comprise rigid backbones, annellated rings, pre-existing double bonds, hydrogen bonds, geminal dialkyl groups, a coordination at metal centers, chiral centers, supramolecular structures.

This access to said class of substances, which is improved and shortened as compared with the previously used methods for preparing cycloalkynes, is important since various cycloalkynes as such are interesting as antibiotics (confer Nicolauo K. C. *Angew. Chem.* 1991, 103, 1453) and can be converted into other macrocyclic products of economic importance such as, e.g., pharmaceuticals, pheromones, agrochemicals, crown ethers, odorous substances, perfume ingredients, or flavoring agents by existing methods.

Scheme 2
Principle of the preparation of macrocyclic cycloalkynes by metathesis of suitable diyne substrates.

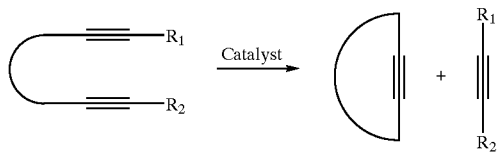

The selectivity of this reaction depends in particular on the structure of the substrates, the used catalyst, the reaction conditions, and the ring strain within the prepared cycloalkyne. The formation of the cycloalkynes is favored by performing the reaction under high dilution in an organic solvent which does not deactivate the catalyst. When determining the concentration of the substrate in the reaction medium, the effective molarity parameter thereof has to be considered (Mandolini, L. *Adv. Phys. Org. Chem.* 1986, 22, 1). According to the present invention, cycloalkadiyne products can also be obtained at higher concentrations by a cyclodimerization of the diyne substrates according to scheme 3.

Scheme 3
Principle of the preparation of macrocyclic cycloalkadiynes by cyclodimerization of suitable diyne substrates.

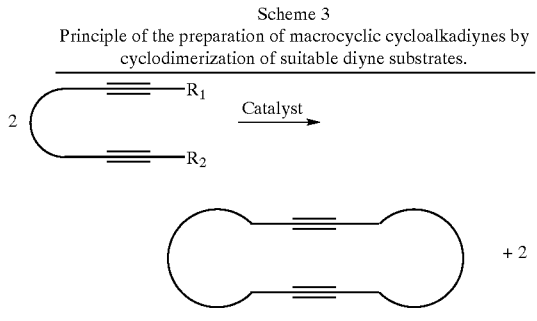

In the present invention all metal compounds being active in alkyne metatheses may be catalysts or pre-catalysts regardless of whether they are initially introduced homogeneously or heterogeneously into the reaction medium. The catalysts can be employed in an isolated form or formed in situ within the reaction medium from suitable precursors. The used amount of catalyst is not critical, with preferred amounts of catalyst being within the range from 0.01–10%, based on the used substrate.

Transition metal alkylidyne complexes, transition metal compounds forming alkylidyne complexes under reaction conditions, and transition metal compounds with metal-metal triple bonds are preferred catalysts or pre-catalysts.

The abbreviations used in the following text indicate: i-Pr=isopropyl; t-Bu=tertiary butyl; Ph=phenyl; acac=acetylacetonate; Ar=aryl; gem=geminal; Me=methyl.

Complexes of the general type $M(\equiv CR^1)(OR^2)_3$ with M=Mo, W
$R^1 = C_1-C_{20}$ alkyl, aryl, alkenyl, alkylthio, dialkylamino, preferably $CMe_3$, Ph
$R^2 = C_1-C_{20}$ alkyl, aryl, preferably $CMe_3$, $CH(CF_3)_2$, $CMe_2CF_3$, $CMe(CF_3)_2$, $C(CF_3)_3$, $C_6H_3Me_2$, $C_6H_3i\text{-}Pr_2$, $C_6H_3t\text{-}Bu_2$ are especially preferred catalysts or pre-catalysts.

Especially preferred catalysts or pre-catalysts are also complexes of the general type $Re(\equiv CR^1)(\equiv NAr)(OR^2)_2$ with
$R^1 = C_1-C_{20}$ alkyl, aryl, alkenyl, preferably $CMe_3$, Ph
Ar=$C_6-C_{20}$ aryl
$R^2 = C_1-C_{20}$ alkyl, aryl, preferably $CMe_3$, $CH(CF_3)_2$, $CMe_2CF_3$, $CMe(CF_3)_2$, $C(CF_3)_3$, $C_6H_3Me_2$, $C_6H_3i\text{-}Pr_2$, $C_6H_3t\text{-}Bu_2$ Especially preferred catalysts or pre-catalysts are also complexes of the general type $(RO)_3M\equiv M(OR)_3$ with M=Mo, W
$R = C_1-C_{20}$ alkyl, aryl, preferably $CMe_3$, $CH(CF_3)_2$, $CMe_2CF_3$, $CMe(CF_3)_2$, $C(CF_3)_3$.

Preferred catalysts formed in situ within the reaction medium result from mixtures of $Mo(CO)_6$ and phenols. Especially preferred catalysts are formed by using electron-deficient phenols such as trifluoromethylphenolf bis(trifluoromethyl)phenol, fluorophenol, difluorophenol, pentafluorophenol, chlorophenol, dichlorophenol ntachlorophenol. The ratio $Mo(CO)_6$: phenol is not critical; preferred ratios $Mo(CO)_6$: phenol are within the range from 1:1 to 1:1000.

Furthermore, preferred catalysts produced in situ within the reaction medium are formed from mixtures of $M[N(R^1)Ar]_3$ and halogen compounds of the $R^2_2EX_2$ or $R^3_3SiX$ types, wherein
M=Mo, W p1 $R^1 = C_1-C_{20}$ alkyl, secondary alkyl (sec-alkyl), tertiary alkyl (t-alkyl), cycloalkyl, preferably t-Bu
Ar=$C_6-C_{20}$ aryl, preferably $C_6H_5$, $C_6H_4Me$, $C_6H_3Me_2$, $C_6H_3(i\text{-}Pr)_2$, $C_6H_3(t\text{-}Bu)_2$, $C_6H_2Me_3$
$R^2$=H, F, Cl, Br, I, $C_{1-20}$ alkyl, aryl
E=C, Si
$R^3 = C_1-C_{20}$ alkyl, aryl, preferably methyl
X=F, Cl, Br, I With respect to compounds of the $M[N(R^1)Ar]_3$ type see: C. E. Laplaza et al., J. Am. Chem. Soc. 1996, 118, 8623.

The diynes used in the present invention as substrates may contain one or several functional groups in the form of substituents on the chain or heteroatoms within the chain. Said substituents comprise inter alia branched or unbranched alkyl rests, aromatic or non-aromatic carbocyclic rings, aromatic or non-aromatic nitrogen, oxygen, sulfur, or phosphorous containing heterocyclic rings, carboxylic acids, esters, ethers, epoxides, silyl ethers, thioethers, thioacetals, disulfides, alcohols, anhydrides, imines, silyl ethers, silylenol ethers, ammonium salts, amines, amides, nitriles, perfluoroalkyl groups, gem-dialkyl groups, alkenes, halogens, ketones, ketals, aldehydes, acetals, carbamates, carbonates, urethanes, ureas, sulfonates, sulfones, sulfonamides, sulfoxides, phosphates, phosphonates, nitro groups, organosilane moieties, or metal centers. The presence of said functional groups within the substrates can favor the formation of the macrocyclic cycloalkyne products. Representative examples are summarized in table 1 and in the examples.

The diynes used as substrates may be conformationally pre-organized for the ring closure by structural elements such as, e.g., chiral centers, hydrogen bonds, supramolecular structures, rigid backbones, coordination at metal centers. Substrates which do not have any one of these structural elements and which are conformationally flexible for this reason may be used as well. The substrates may be present in a supported form.

Diynes with $R_1$, $R_2 \neq H$ are preferred substrates. Especially preferred substrates are diynes in which the moieties $R_1$ and $R_2$ in schemes 2 and 3 are selected such that a low-molecular alkyne $R_1C\equiv CR_2$ (e.g., 2-butyne, 2-hexyne, 3-hexyne) is formed as a by-product of the formation of the macrocyclic cycloalkyne.

The reactions are performed such that the respective substrates are contacted with the homogeneous or heterogeneous catalyst. Normally, this is effected by mixing a solution or suspension of the substrate with a solution or suspension of the catalyst. Depending on the used catalyst and substrate the reaction temperature can be varied, from $-30°$ C. to $+200°$ C. being preferably used. The reaction time is not critical and can be varied between several minutes and several days. The reactions are preferably performed under an inert atmosphere (e.g., argon, nitrogen, helium).

In general, hydrocarbons (e.g., hexane, octane, petroleum ether, toluene, xylenes, cumene, decalin) or halogenated hydrocarbons (e.g., chlorobenzene, bromobenzene, fluorobenzene, trifluoromethylbenzene, dichlorobenzene, trichlorobenzene, tetrachloromethan, 1,2-dichloroethane) are preferred as solvents for the ring-closing diyne metatheses yielding macrocyclic cycloalkynes. When selecting suitable catalysts, other solvents such as, e.g., acetonitrile, tetrahydrofuran, 1,4-dioxane, dimethoxyethane, dimethyl formamide, dimethyl sulfoxide, phenol may be used. Mixtures of said solvents may be used as well.

The reactions can be performed at pressures below atmospheric pressure. Applying a reduced pressure can result in the elimination of volatile by-products $R_1C\equiv CR_2$ and thus increase the obtained cycloalkyne yield. The reduced pressure applicable in each case depends on the specific properties of the substrate, the formed cycloalkyne, the alkyne $R_1C\equiv CR_2$ obtained as by-product according to schemes 2 and 3, the used solvent, and any additives. In addition, the low-molecular by-product R₁C≡CR₂ can be stripped off the reaction mixture by passing an inert gas flow through the reaction mixture, which results in an increase of the cycloalkyne yield.

The recovery of the reaction mixtures and the purification of the products is not critical and depends on the respective physical properties of the produced products and/or the unreacted substrates. Preferred recovery and purification methods are distillation, sublimation, crystallization, chromatography, filtration, and extraction.

The macrocyclic cycloalkynes accessible according to the present invention may be used for the synthesis of numerous resultant products, e.g., by a reduction, oxidation, or cycloaddition of the triple bond and additions to the triple bond. The possibility to convert the macrocyclic cycloalkynes accessible by the present invention into macrocyclic cycloalkenes having uniform configurations of the double bond by suitable reactions (e.g., partial hydrogenation, hydrometalation, carbometalation) is particularly important.

Normally, macrocyclic cycloalkenes having a uniform configuration of the double bond are not accessible by a ring-closing metathesis (RCM) of dienes. In most cases the RCM yields mixtures of the respective (E)- and (Z)-isomers with the (E) isomer being often formed preferably (Schuster M. et al., *Angew. Chem.* 1997, 109, 2125; Fürstner, A. *Topics in Catalysis* 1997, 4, 285; Fürstner, A. et al. *Synthesis* 1997, 792). The present invention, however, enables the selective preparation of macrocyclic, (Z)-configured cycloalkenes by reacting the cycloalkynes obtained from the ring-closing metathesis of diynes using suitable reactions such as, e.g., a partial hydrogenation or hydrometalation/protonation (reviews: March, *J. Advanced Organic Chemistry*, 4th Ed., Wiley, New York, 1992, p 771ff; Marvell, E. N. et al. *Synthesis* 1973, 457; Fürstner, A. et al. *J. Org. Chem.* 1997, 62, 2332). Here, the cycloalkynes accessible by the present invention can initially be isolated and thereafter converted into the (Z)-configured cycloalkene according to a suitable method. Alternatively, the formation of the macrocyclic cycloalkyne by a ring-closing alkyne metathesis of a diyne substrate and the conversion thereof into a macrocyclic, (Z)-configured cycloalkene in one single reaction batch is performed successively within the meaning of an integrated chemical method.

Macrocyclic cycloalkenes having a (Z)-configured double bond are often used as antibiotics, pharmaceuticals for human or veterinary medicine, pheromones, odorous substances, perfume ingredients etc. A representative example for the synthesis of a pharmaceutically relevant macrocyclic product by oxidation of a macrocyclic cycloalkene are epothilone and analogues of this compound. If the (Z)-configured cycloalkene required for the synthesis of epothilone or the analogues thereof is prepared by RCM, usually (E)/(Z)-mixtures are obtained, however, only the respective (Z)-alkenes thereof can be converted into epothilone or the analogues of this natural substance having the correct configuration of the stereogeneous centers of the formed epoxides by epoxidizing the double bond (Nicolaou, K. C. et al. *Angew. Chem.* 1996, 108, 2554; Meng, D. *J. Am. Chem. Soc.* 1997, 119, 2733; Taylor, R. E. *Tetrahedron Lett.* 1997, 2061; Schinzer, D. et al. *Angew. Chem.* 1997, 109, 543; Yang, Z. *Angew. Chem.* 1997, 109, 170; Bertinato, P. *J. Org. Chem.* 1996, 61, 8000; Nicolaou, K. C. et al. *J. Am. Chem. Soc.* 1997, 119, 7960; Nicolaou K. C. et al. *Nature* 1997, 387, 268; Nicolaou, K. C. et al. *Chem. Eur. J.* 1997, 3, 1957; Nicolaou K. C. et al., *Angew. Chem.* 1997, 109, 2181). Said synthesis and similar syntheses may be designed stereoselectively and consequently considerabely improved by forming the macrocyclic cycloalkyne and subsequently partially reducing said cycloalkyne to the (Z)-cycloalkene.

The examples specified hereinafter describe prototypical ring-closing reactions of diynes to macrocyclic products by alkyne metathesis catalysts under preferred conditions, however, said examples should by no means limit the scope, the scope of application, or the advantages of the present invention.

EXAMPLE 1

Cyclization of Hexanedicarboxylic Acid bis(3-pentynyl) Ester

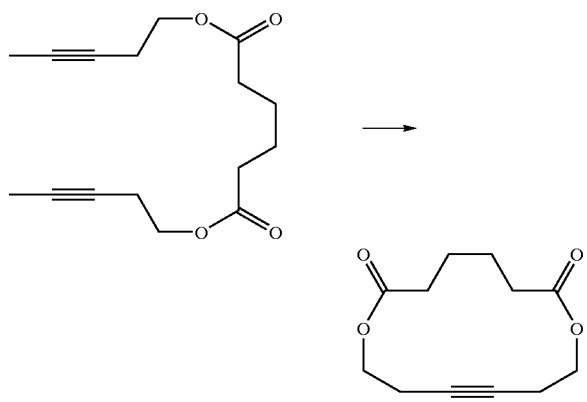

In an apparatus consisting of a two-neck flask with an attached distillation bridge and a receiver cooled to −78° C., W(≡CCMe₃)(OCMe₃)₃ (8 mg) is added to a solution of hexanedicarboxylic acid bis(3-pentynyl) ester (155 mg, 0.56 mmol) in 1,2,4-trichlorobenzene (30 ml). The apparatus is evacuated to 20 mbar and the reaction mixture is heated to 80° C. After 4 h additional W(≡CCMe₃)(OCMe₃)₃ (8 mg) is added, and thereafter the solution is stirred at 80° C./20 mbar for 13 h. Distilling off the solvent in the high vacuum and purifying the residue by column chromatography (eluent hexane/ethyl acetate 4:1) yields the cycloalkyne as colorless crystals (100 mg, 79%). Mp=106–107° C. $^1$H NMR: δ=4.14 (t, 4H, J=5.5), 2.53 (t, 4H, J=5.6), 2.40 (m, 4H), 1.76 (m, 4H). $^{13}$C NMR: δ=173.0, 77.8, 62.4, 34.8, 24.9, 19.0. MS, m/z (rel intensity): 224 (<1), [M⁺], 179 (<1), 166 (1), 152 (1), 137 (1), 129 (3), 111 (7), 101 (4), 78 (100), 66 (21), 55 (10), 41 (8). C₁₂H₁₆O₄ (224.3) calcd.: C 64.24. H 7.18; found: C 64.14. H 7.15.

EXAMPLE 2

Cyclization of Hexanedicarboxylic Acid bis(3-pentynyl) Ester

A solution of hexanedicarboxylic acid bis(3-pentynyl) ester (105 mg) and W(≡CCMe₃)(OCMe₃)₃ (11 mg) in toluene (20 ml) is stirred under Ar at 80° C. for 1 h. The solvent is distilled off in the vacuum, the remaining residue is purified by column chromatography (hexane/ethyl acetate 4/1), and the desired cycloalkyne is obtained in form of colorless crystals (59 mg, 69%). The analytical data are as specified in example 1.

EXAMPLE 3

Cyclization of Hexanedicarboxylic Acid bis(3-pentynyl) Ester

A solution of hexanedicarboxylic acid bis(3-pentynyl) ester (121 mg) and W(≡CCMe₃)(OCMe₃)₃ (12 mg) in chlorobenzene (20 ml) is stirred under Ar at 80° C. for 2 h. The solvent is distilled off in the vacuum, the remaining residue is purified by column chromatography (hexane/ethyl acetate 4/1), and the desired cycloalkyne is obtained in form of colorless crystals (70 mg, 73%). The analytical data are as specified in example 1.

EXAMPLE 4

Cyclization and Cyclodimerization of 10-dodecyne-1-yl 10-dodecynoate

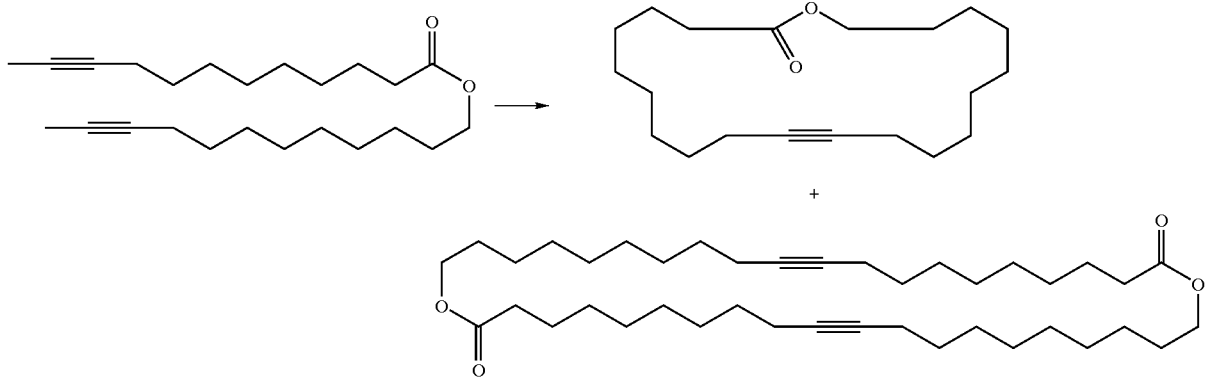

A solution of 10-dodecyne-1-yl 10-dodecynoate (139 mg, 0.39 mmol) and W($\equiv$CCMe$_3$)(OCMe$_3$)$_3$ (9 mg) in chlorobenzene (50 ml) is stirred at 80° C. for 10 h. After distilling off the solvent and a column chromatography of the residue (hexane/ethyl acetate 20/1) the cycloalkyne is obtained in form of colorless crystals (62 mg, 52%) and the cycloalkadiyne (cyclodimerization product) in form of a colorless, crystalline product.

Data of the cycloalkyne: $^1$H NMR: δ=4.12 (t, 2H, J=5.8), 2.32 (t, 2H, J=6.8), 2.16 (m, 4H), 1.64 (m, 4H), [1.46 (m), 1.32 (m); 18H]. $^{13}$C NMR: δ=173.8, 80.7, 80.5, 63.9, 34.6, 29.39, 29.36, 29.2, 28.8 (2C), 28.6 (2C), 28.4 (2C), 28.3, 28.1, 25.9, 25.3, 18.5, 18.4. MS, m/z (rel. intensity): 306 (35) [M$^+$], 277 (4), 264 (5), 250 (3), 209 (6), 192 (19), 178 (34), 164 (40), 149 (24), 135 (54), 121 (61), 107 (43), 95, (71), 81 (97), 67 (98), 55 (100), 41 (82), 29 (25). C$_{20}$H$_{34}$O$_2$ (306.5) calcd.: C 78.37. H 11.19; found: C 77.55. H 11.07.

Data of the cycloalkadiyne: $^1$H NMR: δ=4.07 (t, 4H, J=6.6), 2.29 (t, 4H, J=7.4), 2.14 (m, 8H), 1.62 (m, 8H), 1.47 (m, 8H), 1.4–1.2 (36H). $^{13}$C NMR: δ=173.9, 80.27, 80.25, 64.3, 34.4, 29.3, 29.1, 29.06, 28.98, 28.96, 28.88, 28.62, 28.57, 25.9, 25.0, 18.7. MS, m/z (rel. intensity): 612 (99) [M$^+$], 584 (7), 557 (5), 515 (6), 469 (5), 401 (8), 387 (11), 373 (13), 359 (18), 345 (19), 147 (16), 135 (26), 121 (32), 107 (33), 95, (65), 81 (88), 67 (87), 55 (100).

EXAMPLE 5

Cyclization of N,N-bis(10dodecinoyl)ethane-1,2-diamine

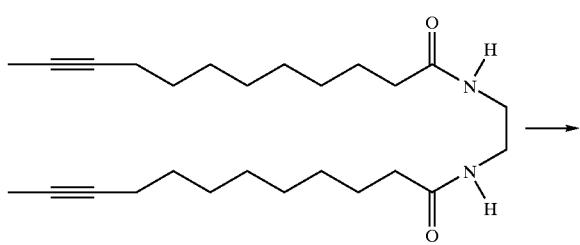

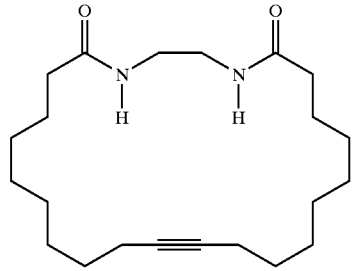

A suspension of N,N-bis(10dodecinoyl)ethane-1,2-diamine (142 mg, 0,34 mmol) and W($\equiv$CCMe$_3$)(OCMe$_3$)$_3$ (8 mg) in chlorobenzene (20 ml) is stirred at 80° C. for 3 h. After distilling off the solvent the cycloalkyne is obtained. An analytically pure sample is obtained by extracting the catalyst out of the product. MS m/z (rel. intensity): 362 (82) [M$^+$], 334 (17), 319 (9), 303 (8), 279 (7), 265 (7), 249 (9), 237 (16), 221, (22), 206 (14), 178 (13), 168 (13), 154 (10), 135 (14), 126 (10), 95 (40), 81 (51), 67 (67), 55 (91), 44 (79), 41 (73), 30 (100).

EXAMPLE 6

Cyclization of Hexanedicarboxylic acid bis(3-pentynyl) Ester in THF

A solution of hexanedicarboxylic acid bis(3-pentynyl) ester (89 mg) and W($\equiv$CCMe$_3$)(OCMe$_3$)$_3$ (18 mg) in tetrahydrofuran (15 ml) is refluxed under Ar for 22 h. The solvent is distilled off in the vacuum, the remaining residue is purified by column chromatography (hexane/ethyl acetate 4/1), and the desired cycloalkyne is obtained in form of colorless crystals (46 mg, 64%). The analytical data are as specified in example 1.

EXAMPLE 7

Cyclization of Hexanedicarboxylic Acid bis(3-pentynyl) Ester Using W($\equiv$CPh)(OCMe$_3$)$_3$ A solution of hexanedicarboxylic acid bis(3-pentynyl) ester (271 mg) and W($\equiv$CPh)(OCMe$_3$)$_3$ (25 mg) in toluene (30 ml) is heated under Ar at 80° C. for 1 h. The solvent is distilled off in the vacuum, the remaining residue is purified by column chromatography (hexane/ethyl acetate 4/1), and the desired cycloalkyne is obtained in form of colorless crystals (134 mg, 61%) The analytical data are as specified in example 1.

EXAMPLE 8

Cyclization by Using Mo(CO)$_6$/p-chlorophenol as Alkyne Metathesis Catalyst

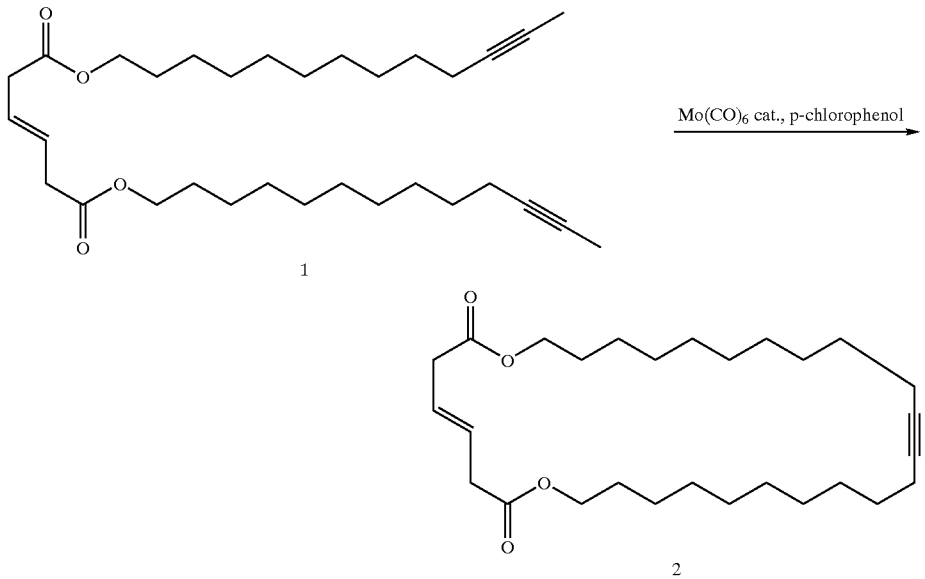

A solution of the diyne substrate 1 (200 mg), Mo(CO)$_6$ (5 mg), and p-chlorophenol (55 mg) in chlorobenzene (75 ml) is heated to 120° C. for 3 h. During the reaction a slight argon flow is passed through the reaction mixture. In order to recover the product, the volatile components are distilled off under vacuum and the remaining residue is purified by column chromatography (hexane/t-butyl methyl ether 20/1). The 30-membered cycloalkyne 2 is obtained in form of a colorless solid (126 mg, 70%).

$^1$H-NMR: δ=5.63 (dt, 2H), 4.01 (t, 4H), 3.00 (dd, 4H, J=4, 1.6), 2.08 (t, 4H, J=6.5), 1.36 (m, 8H), 1.23 (m, 18H). $^{13}$C-NMR: δ=171.8, 126.3, 80.8, 65.2, 38.6, 29.7, 29.6, 29.5, 29.4, 29.1, 28.9, 28.8, 26.2, 19.0.

EXAMPLE 9

Preparation of Ambrettolide by a Diyne Metathesis and a Subsequent Partial Hydrogenation A solution of the diyne 3 (1.0 g), Mo(CO)$_6$ (42 mg), and p-chlorophenol (425 mg) in chlorobenzene (150 ml) is heated to 120° C. for 19 h. During the reaction a slight argon flow is passed through the reaction mixture from a gas inlet.

In order to recover the product, the volatile components are distilled off under vacuum and the remaining residue is purified by column chromatography (eluent hexane/t-butyl methyl ether 20/1). The cycloalkyne 4 is obtained as a colorless syrup (568 mg, 69%) with the following analytical data:

$^1$H-NMR: δ=4.10 (t, 2H, J=5.2), 2.28 (t, 2H, J=7), 2.13 (m, 4H), 1.60 (m, 4H), 1.15 (m, 14H). $^{13}$C-NMR: δ=174.4, 80.7, 80.6, 64.3, 35.0, 28.8, 28.7, 28.5, 28.46, 28.40, 27.4, 25.3, 19.1, 18.9.

A reaction mixture consisting of the cycloalkyne 4 (154 mg), quinoline (60 μl), and Lindlar catalyst (=5% Pd on calcium carbonate, contaminated with lead) (60 mg) in hexane (3 ml) is stirred under an hydrogen atmosphere (1 atm) for 1.5 h. The catalyst is filtered off, the filtrate is washed with aqueous HCl (5%), the organic phase is dried over Na$_2$SO$_4$, and the solvent is removed in the vacuum. A subsequent column chromatography (eluent hexane/t-butyl methyl ether 20/1) yields abrettolide 5 (138 mg, 92%).

$^{13}$C-NMR: δ=174.3, 130.5, 130.4, 64.1, 34.9, 29.8, 29.1, 29.0, 28.9, 28.8, 28.7, 28.0, 27.3, 27.1, 25.7, 25.6.

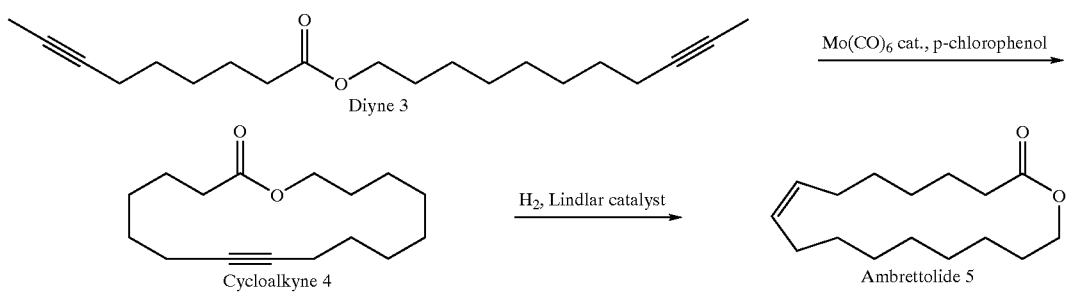

EXAMPLE 10

Cyclization of Hexanedicarboxylic Acid bis(3-pentynyl) Ester Using Mo[N(t-Bu)(3,5-C$_6$H$_3$Me$_2$)]$_3$/ CH$_2$Cl$_2$ as Diyne Metathesis Catalyst A reaction mixture consisting of hexanedicarboxylic acid bis(3-pentynyl) ester (60 mg) and Mo[N(t-Bu)(3,5-C$_6$H$_3$Me$_2$)]$_3$ (13.5 mg) (prepared according to the literature: C. E. Laplaza et al. *J. Am. Chem. Soc.* 1996, 118, 8623) in toluene (15 ml) and CH$_2$Cl$_2$ (50 µl) is heated under argon for 19 h. The solvent is distilled off in the vacuum, the remaining residue is purified by column chromatography (hexane/ethyl acetate 4/1) and the desired cycloalkyne is obtained in form of colorless crystals (38.8 mg, 80%). The analytical data are as specified in example 1. Instead of CH$_2$Cl$_2$ also CHCl$_3$, CCl$_4$, CH$_2$Br$_2$, CH$_2$I$_2$, α,α-dichlorotoluene, or trimethylchlorosilane can be used to activate the molybdenum component. Similarly, the reaction can be performed in dichloromethane as the solvent.

EXAMPLE 11

Diyne Metathesis Using Mo[N(t-Bu)(3,5-C$_6$H$_3$Me$_2$)]$_3$/CH$_2$Cl$_2$

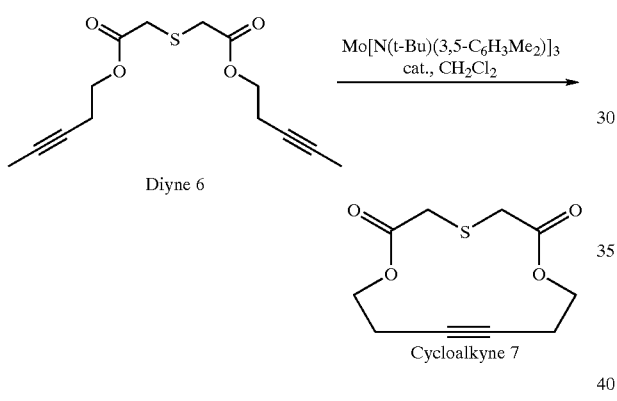

A reaction mixture consisting of diyne 6 (91.5 mg) and Mo[N(t-Bu)(3,5-C$_6$H$_3$Me$_2$)]$_3$ (20.2 mg) (prepared according to the literature: C. E. Laplaza et al. *J. Am. Chem. Soc.* 1996, 118, 8623) in toluene (15 ml) and CH$_2$Cl$_2$ (50 µl) is heated to 80° C. under argon for 22 h. The solvent is distilled off in the vacuum, the remaining residue is purified by column chromatography (hexane/ethyl acetate 8/1) and the desired cycloalkyne 7 is obtained in form of a colorless syrup (62 mg, 84%). Analytical data:

$^1$H NMR: δ=4.28 (t, 4H, J=5.4), 3.43 (s, 4H), 2.49 (t, 4H). $^{13}$C NMR: δ=169.4, 78.1, 62.9, 34.6 (2×), 19.6. MS: m/z (rel. intensity): 228 (56, [M$^+$]), 78 (100).

EXAMPLE 12

Diyne Metathesis Using Mo[N(t-Bu)(3,5-C$_6$H$_3$Me$_2$]$_3$/CH$_2$Cl$_2$

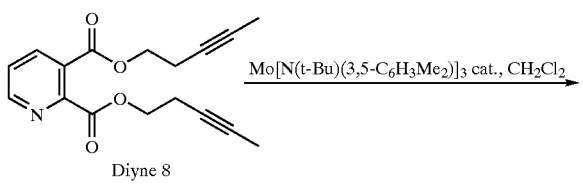

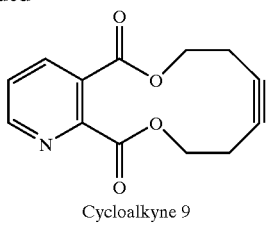

Cycloalkyne 9

A reaction mixture consisting of diyne 8 (511 mg) and Mo[N(t-Bu)(3,5-C$_6$H$_3$Me$_2$)]$_3$ (104.4 mg) (prepared according to the literature: C. E. Laplaza et al. *J. Am. Chem. Soc.* 1996, 118, 8623) in toluene (82 ml) and CH$_2$Cl$_2$ (160 µl) is heated to 80° C. under argon for 20 h. The solvent is distilled off in the vacuum, the remaining residue is purified by column chromatography (hexane/ethyl acetate 4/1) and the desired cycloalkyne 9 is obtained in form of a colorless syrup (369 mg, 88%). Analytical data: $^1$H NMR: δ=8.76 (dd, 1 H, J=4.9, 1.9), 8.12 (dd, 1 H, J=7.9, 1.5), 7.52 (dd, 1 H, J=4.9), 4.63 (t, 2H, J=5.5), 4.42 (t, 2H, J=5.6), 2.57 (m, 4H). $^{13}$C NMR: δ=166.1, 165.8, 151.1, 151.0, 137.1, 128.7, 125.1, 79.2, 78.8, 63.4, 63.1, 20.0, 19.4). MS: m/z (rel. intensity): 245 (2, [M$^+$]), 78 (100).

EXAMPLE 13

Preparation of a 11-membered Cycloalkyne: Cyclization and Cyclodimerization of Dimethylmalonic Acid bis(3-pentynyl) Ester

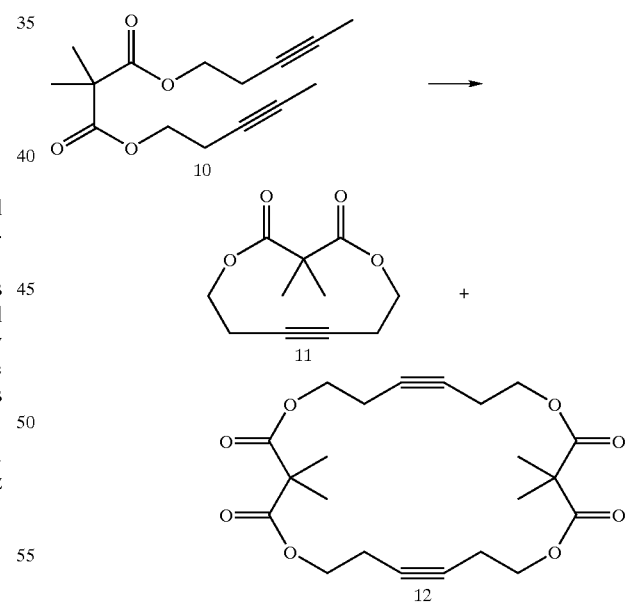

A solution of dimethylmalonic acid bis(3-pentynyl) ester 10 (262 mg) and W(≡CCMe$_3$)(OCMe$_3$)$_3$ (28 mg) in chlorobenzene (60 ml) is stirred under argon at 80° C. for 1 h. After distilling off the solvent at 12 mbar and a purification by of the residue column chromatography the waxy cycloalkyne 11 (97 mg, 47%) and crystalline cycloalkadiyne 12 (87 mg, 42%) is obtained and a small amount of Diyne 10 (37 mg, 14%) is recovered.

Data of the cycloalkyne 11: $^1$H NMR: δ=4.29 (t, 4H, J=5.8), 2.43 (t, 4H), 1.43 (s, 6H). $^{13}$C NMR: δ=172.0, 79.8, 61.8, 50.0, 22.1, 19.7,.–MS, m/z (rel. intensity): 152 (2) [M–58], 137 (3), 111 (5), 87 (5), 78 (100), 70 (49), 66 (17), 65 (18), 41 (16).–C$_{11}$H$_{14}$O$_4$ (210.2) calcd: C 62.85. H 6.71; found: C 63.01. H 6 67.

Data of the cycloalkadiyne 12: $^1$H NMR: δ=4.15 (t, 8H, J=6.8), 2.53 (t, 8H), 1.43 (s, 12H). $^{13}$C NMR: δ=172.4, 77.3, 63.5, 49.4, 22.5, 18.8.–MS, m/z (rel. intensity): 420 (5) [M$^+$], 174 (8), 156 (48), 141 (14), 115 (7), 87 (10), 78 (100), 70 (34), 69 (31), 66 (13), 65 (11), 41 (19).

TABLE 1

Synthesis of functionalized, macrocyclic cycloalkynes by ring-closing metathesis of diynes using W(≡CCMe$_3$)(OCMe$_3$)$_3$ as a catalyst.

| Substrate | Product | Yield |
|---|---|---|
| | | 52% |
| | | 79% |
| | | 69% |
| | | 52% |
| | | 97% |

TABLE 1-continued

Synthesis of functionalized, macrocyclic cycloalkynes by ring-closing metathesis of diynes using W(≡CCMe₃)(OCMe₃)₃ as a catalyst.

| Substrate | Product | Yield |
|---|---|---|
| | | >90% |
| | | 52% |
| | | 55% |
| | | 20% |

What is claimed is:

1. A process for the preparation of a carbocyclic or heterocyclic compound having 9 or more ring atoms by a ring-closing metathesis reaction, said process comprising reacting one or more diyne substrates in a reaction medium in the presence of one or several alkyne metathesis catalysts present homogeneously or heterogeneously in the reaction medium.

2. The process according to claim 1, which produces a carbocyclic or heterocyclic compound having 12 or more ring atoms.

3. The process according to claim 1, wherein the one or more diyne substrates contain one or several functional groups in the form of substituents on the chain or heteroatoms within the chain; said functional groups comprise branched or unbranched alkyl moieties, aromatic or non-aromatic carbocyclic rings, aromatic or non-aromatic nitrogen, oxygen, sulfur or phosphorus containing heterocyclic rings, carboxylic acids, esters, ethers, epoxides, silyl ethers, thioethers, thioacetals, disulfides, alcohols, anhydrides, imines, silyl ethers, silylenol ethers, ammonium salts, amines, amides, nitriles, perfluoroalkyl groups, gem-dialkyl groups, alkenes, halogens, ketones, ketals, aldehydes, acetals, carbamates, carbonates, urethanes, ureas, sulfonates, sulfones, sulfonamides, sulfoxides, phosphates, phosphonates, nitro groups, organosilane moieties, or metal centers.

4. The process according to claim 1, wherein the alkyne metathesis catalyst used is a transition metal alkylidyne complex.

5. The process according to claim 4, wherein the transition metal alkylidyne complex is formed in situ within the reaction medium.

6. The process according to claim 4, wherein the transition metal alkylidyne complex used as the catalyst is a compound of the type M(≡CR¹)(OR²)₃, wherein:

M=Mo, or W;

$R^1$=$C_1$–$C_{20}$ alkyl, aryl, alkenyl, alkylthio, or dialkylamino; and $R^2$=$C_1$–$C_{20}$ alkyl, or aryl.

7. The process according to claim 6, wherein:

M=W $R^1$=CMe$_3$, or Ph; and $R^2$=CMe$_3$, CH(CF$_3$)$_2$, CMe$_2$CF$_3$, CMe(CF$_3$)$_2$, C(CF$_3$)$_3$, C$_6$H$_3$Me$_2$, C$_6$H$_3$i-Pr$_2$, or C$_6$H$_3$t-Bu$_2$.

8. The process according to claim 4, wherein the transition metal alkylidyne complex used as the catalyst is a compound of the type Re(≡CR$^1$)(=NAr)(OR$^2$)$_2$, wherein:

$R^1$=C$_1$–C$_{20}$ alkyl, aryl, or alkenyl;

Ar=C$_6$–C$_{20}$ aryl; and $R^2$=C$_1$–C$_{20}$ alkyl, or aryl.

9. The process according to claim 8, wherein:

$R^1$=CMe$_3$, or Ph;

Ar=C$_6$–C$_{20}$ aryl; and $R^2$=CMe$_3$, CH(CF$_3$)$_2$, CMe$_2$CF$_3$, CMe(CF3), C(CF$_3$)$_3$, C$_6$H$_3$Me$_2$, C$_6$H$_3$i-Pr$_2$, or C$_6$H$_3$t-BU$_2$.

10. The process according to claim 1, wherein the alkyne metathesis catalyst used is a complex having a metal≡metal triple bond.

11. The process according to claim 10, wherein the alkyne metathesis catalyst used is a complex of the type (RO)$_3$M≡M(OR)$_3$, wherein:

M=Mo, or W; and

R=C$_1$–C$_{20}$ alkyl.

12. The process according to claim 11, wherein:

R=CMe$_3$, CH(CF$_3$)$_2$, CMe$_2$CF$_3$, CMe(CF$_3$)$_2$, or C(CF$_3$)$_3$.

13. The process according to claim 1, wherein the alkyne metathesis catalyst is formed from M[N(R$^1$)Ar]$_3$ and a halogen compound of the type R$^2$$_2$EX$_2$ or R$^3$$_3$SiX; wherein:

M=Mo, or W;

$R^1$=C$_1$–C$_{20}$ alkyl, sec-alkyl, t-alkyl, or cycloalkyl;

Ar=C$_6$–C$_{20}$ aryl;

$R^2$=H, F, Cl, Br, I, C$_{1-20}$ alkyl, or aryl;

E=C, or Si;

$R^3$=C$_1$–C$_{20}$ alkyl, or aryl; and

X=F, Cl, Br, or I.

14. The process according to claim 13, wherein:

M=Mo;

$R^1$=t-Bu, or i-Pr;

Ar=C$_6$H$_5$, C$_5$H$_4$Me, C$_6$H$_3$Me$_2$, C$_6$H$_3$(iPr)$_2$, C$_6$H$_3$(t-Bu)$_2$, or C$_6$H$_2$Me$_3$;

$R^2$=H, F, Cl, Br, I, or C$_6$CH$_5$; and $R^3$=Me, t-Bu, or i-Pr.

15. The process according to claim 1, wherein the one or more diyne substrates are conformationally pre-organized for the ring closure by one or several structural elements; and said structural elements comprise chiral centers, hydrogen bonds, supramolecular structures, rigid backbones, or a coordination to metal centers.

16. The process according to claim 1, wherein the one or more diyne substrates are conformationally flexible.

17. The process according to claim 1, wherein the one or more diyne substrates are used in a supported form.

18. The process according to claim 1, which produces a macrocyclic cycloalkyne, and wherein the formation of the macrocyclic cycloalkyne is favored by selecting the concentration of the one or more diyne substrates in solution.

19. The process according to claim 1, wherein the reaction is carried out at a pressure below atmospheric pressure.

20. The process according to claim 1, wherein side products are eliminated by passing an inert gas flow through the reaction medium.

21. The process according to claim 1, wherein the activity of the catalyst or catalysts used is increased by additives.

22. The process according to claim 21, wherein phenols, geminal dihalogenalkanes (gem-dihalogenalkanes) or halogensilanes are used as additives.

23. The process according to claim 22, wherein phenol, trifluoromethylphenol, bis(trifluoromethyl)phenol, fluorophenol, difluorophenol, pentafluorophenol, chlorophenol, dichlorophenol, pentachlorophenol, dichloromethane, dibromomethane, diiodomethane, chloroform, bromoform, iodoform, tetrachlorocarbon, tetrabromocarbon, tetraiodocarbon, α, α-dichlorotoluene, trimethylchlorosilane, dimethyldichlorosilane, trimethylbromosilane, dimethyl(t-butyl)chlorosilane, or dimethylphenylchlorosilane are used as additives.

24. The process according to claim 1, wherein the one or more diyne substrates are cyclodimerized.

25. A process for the preparation of a carbocyclic or heterocyclic cycloalkene having 9 or more ring atoms, said process comprising preparing a cycloalkyne according to the process according to claim 1, and selectively converting said cycloalkyne into a cycloalkene having a uniform double bond configuration.

26. The process according to claim 25, which produces a cycloalkene having a (Z)-configured double bond.

27. A process for the preparation of epothilone or an epothilone analog, said process comprising preparing a functionalized cycloalkyne according to the process according to claim 2 and thereafter converting said functionalized cycloalkyne into epothilone or an epothilone analog.

28. The process according to claim 1, wherein the carbocyclic or heterocyclic compound produced is one of antibiotics, pharmaceuticals for human or veterinary medicine, pheromones, crown ethers, odorous substances, perfume ingredients, or flavoring agents.

29. The process according to claim 1, wherein the alkyne methathesis catalyst is a Mo-carbonyl complex.

30. The process according to claim 29, wherein the Mo-carbonyl complex is Mo(CO)$_6$.

\* \* \* \* \*